United States Patent
Qin et al.

(10) Patent No.: US 10,017,602 B2
(45) Date of Patent: Jul. 10, 2018

(54) CYCLIC ACETAL, CYCLIC KETAL DIAMINES EPOXY CURING AGENTS AND DEGRADABLE POLYMERS AND COMPOSITES BASED THEREON

(71) Applicant: ADESSO ADVANCED MATERIALS WUXI CO., LTD., Wuxi New District (CN)

(72) Inventors: Bing Qin, Shanghai (CN); Xin Li, Cottenham (GB); Bo Liang, Plainsboro, NJ (US)

(73) Assignee: ADESSO AVANCED MATERIALS WUHU CO., LTD., Wuhu (CN)

( * ) Notice: Subject to any disclaimer, the term of this patent is extended or adjusted under 35 U.S.C. 154(b) by 0 days.

(21) Appl. No.: 14/781,264

(22) PCT Filed: Apr. 18, 2014

(86) PCT No.: PCT/CN2014/075696
§ 371 (c)(1),
(2) Date: Sep. 29, 2015

(87) PCT Pub. No.: WO2014/169846
PCT Pub. Date: Oct. 23, 2014

(65) Prior Publication Data
US 2016/0046760 A1    Feb. 18, 2016

(30) Foreign Application Priority Data

Apr. 18, 2013 (CN) .......................... 2013 1 0136121
Apr. 18, 2013 (CN) .......................... 2013 1 0137251

(51) Int. Cl.
| | | |
|---|---|---|
| C08G 59/50 | (2006.01) | |
| C07D 317/28 | (2006.01) | |
| C08J 11/24 | (2006.01) | |
| C08K 7/06 | (2006.01) | |
| D01F 9/12 | (2006.01) | |

(52) U.S. Cl.
CPC ....... *C08G 59/5046* (2013.01); *C07D 317/28* (2013.01); *C08J 11/24* (2013.01); *C08K 7/06* (2013.01); *D01F 9/12* (2013.01)

(58) Field of Classification Search
CPC .... C07D 317/28; C08G 59/5046; C08J 11/24; C08K 7/06; D01F 9/12
USPC .......................................................... 521/40
See application file for complete search history.

(56) References Cited

U.S. PATENT DOCUMENTS

| | | | | |
|---|---|---|---|---|
| 2,439,969 A | * | 4/1948 | Fourneau ............. | C07D 317/28 549/451 |
| 4,668,700 A | * | 5/1987 | Kr/a/ mer .............. | A01N 43/28 504/219 |
| 5,395,947 A | * | 3/1995 | Kim .................... | C07F 15/0093 549/206 |

FOREIGN PATENT DOCUMENTS

| | | | |
|---|---|---|---|
| CN | 101870686 | * | 10/2010 |
| CN | 101870686 A | | 10/2010 |

OTHER PUBLICATIONS

Machine translation of CN101870686, Rupei Tang, Oct. 2010.*
C. Ramirez et al. Study of an Epoxy System Cured with Different Diamines by Differential Scanning Calorimetry, Journal of Applied Polymer Science, Dec. 31, 20117, vol. 103, pp. 1759-1768.

* cited by examiner

*Primary Examiner* — Frances Tischler
(74) *Attorney, Agent, or Firm* — Weisun Rao; Greeberg Traurig, LLP

(57) ABSTRACT

The present invention provides, among others, compounds of the following formula which can be used as degradable curing agents, methods for preparing the compounds, degradable polymers and reinforced composites, methods for degrading and recycling the polymers and composites.

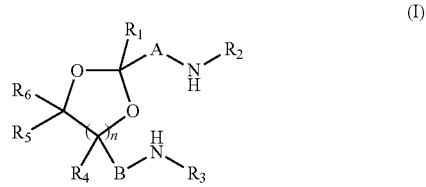

(I)

12 Claims, No Drawings

CYCLIC ACETAL, CYCLIC KETAL DIAMINES EPOXY CURING AGENTS AND DEGRADABLE POLYMERS AND COMPOSITES BASED THEREON

CROSS-REFERENCE TO RELATED APPLICATIONS

This application is a U.S. national phase application of international application No. PCT/CN2014/075696, filed on Apr. 18, 2014, which claims priority to and benefit of Chinese Application No. 201310136121.4 and Chinese Application No. 201310137251. X, both filed on Apr. 18, 2013, the contents of which are incorporated herein by reference in their entireties.

FILED OF THE INVENTION

This application is in general in the field of adhesives, composite materials and epoxy compositions, and more specifically relates to novel cyclic acetal, cyclic ketal diamines epoxy curing agents, and degradable polymers and composites based thereon.

BACKGROUND OF THE INVENTION

Epoxies are an important class of thermosetting polymers. They have diverse applications including adhesives, structural materials, paints coatings, potting, printed circuit boards, microelectronic encapsulation, the aerospace industry, and other consumer goods. Epoxy resins are hardened or cured by a cross-linking reaction using one of three methods. The chemistry of epoxy curing is explained in great detail in the Handbook of Composites (edited by S.T. Peters, Chapter 3, pp 48-74, published by Chapman & Hall, 1998). The properties and applications of cured resin are greatly influenced by the choice of the hardener formulation or the method of curing.

One method is simply the reaction of the epoxy resin with itself (i.e. homopolymerization) via a ring-opening polymerization mechanism of the epoxy groups. The self-curing of epoxy resins usually requires an elevated temperature but can be initiated with either a Lewis acid or a Lewis base catalyst (as opposed to a curing agent).

In the second method, the epoxy resin is cured with a cyclic acid anhydride. The anhydride can react with the epoxy group, pendant hydroxyls, or residual water to form a carboxylate intermediate, which then reacts with the epoxy group, causing a self-perpetuating reaction between the anhydride and the epoxy resin. Catalytic amounts of tertiary amines are commonly used as additives as they facilitate the opening of the anhydride. Anhydride epoxy formulations do not readily cure at room temperature, and generally require anelevated temperature of 80-150° C.

In the third method, the epoxy resin reacts in the ambient with polyvalent nucleophiles such as polyamines to form a polymeric network of essentially infinite molecular weight.

Polyamines of the general formula ($NH_2$—R—$NH_2$) give cold curing compositions. The ring opening of the epoxy ring with a primary or secondary amine generates a stable C—N bond. Epoxy groups will react with potentially every amine containing an active hydrogen atom, so that a simple diamine ($NH_2$—R—$NH_2$) acts as a tetrafunctional cross-linker and reacts with four epoxy groups. Similar to amines, polythiol compounds (HS—R—SH) also react with epoxy rings to form C—S bonds. The reaction of the thiol group with the epoxy group is greatly facilitated by the presence of a catalytic amount of base, such as a tertiary amine. A simple dithiol compound (HS—R—SH) serves only as difunctional chain extender since a primary thiol contains only one active hydrogen atom, but polythiol compounds with a functionality greater than three serve as cross-linkers. Polythiol hardeners also allow for ambient curing compositions. Faster setting formulations, which are commonly sold as two-pack glues in hardware stores, usually contain polythiol hardeners or both polythiol and polyamine hardeners.

By far, the most common epoxy formulations consist of a diepoxide ("resin") and a polyamine ("hardener") to form a polymeric network of essentially infinite molecular weight. The combination of "resin and hardener" is sometimes referred to as "cured epoxy," "cured resin," or simply "resin" or "epoxy." The widespread utility of such epoxy formulations is due to their excellent processability prior to curing and their excellent post-cure adhesion, mechanical strength, thermal profile, electronic properties, chemical resistance, etc. Furthermore, the high-density, infusible three-dimensional network of epoxies makes it an extremely robust material, resulting in it being the material of choice for many long-term applications. For instance, epoxy resin, due to its excellent physical and mechanical properties, electrical insulation, and adhesive performance, is widely used in composite materials, casting parts, electronics, coating, etc. At the same time, this durability makes its removal, recycling and reworkability notoriously difficult, raising concerns about the longevity of epoxy-based materials in the environment. The cross-linking reactions that occur with two convertibly used component epoxies are essentially irreversible. Therefore, the material cannot be melted and reshaped without decomposition of the material. The ordinary consumer is also aware of the intractability of epoxy adhesives and coatings; internet message boards are replete with postings and complaints on how to remove epoxy that has spilled on unwanted places or mistakenly bonded items together. Thus, there exists a need for new epoxy formulations that retain the remarkable physical properties of classical epoxies, but can be disassembled in a controlled and mild manner when desired, without damaging the underlying structure.

As epoxy adhesives are used for the assembly of a variety of common items and epoxies serve as the matrix materials for a variety of structural materials and composites, the development of such a "reworkable" material would have implications in recycling, recovery, and waste disposal. Furthermore, an easily removable epoxy could expand the use of epoxies to new consumer markets. For example, joints could be bonded with epoxy glue and any spill-over could be easily removed, even post-curing, while the joint remains bonded. As another example, epoxy based paints and varnishes could be more easily removed.

The intractability of a cured resin stems, in part, from its highly cross-linked network. If the links in the three-dimensional network can be cleaved under controlled conditions, the network can be disassembled into smaller, soluble molecules and/or polymer, therefore removing the cured resin stem. In principal, this can be accomplished through use of either a dissolvable resin or a curing agent that contains a bond capable of cleavage under a specific set of conditions. In the limited amount of prior art on this topic, the majority has focused on cleavable groups in the resin component. Epoxy formulations that possess cleavable linkages in the hardener, are particularly attractive, as those skilled in the art realize that a great deal of more flexibility exists with regard to the constituents in a hardener component, due to the resin components in most epoxies are based on bisphenol digylcidly ether (BPADGE).

Epoxy prepreg is a compound system composed of epoxy resin, curing system and the reinforcing fiber, the resin system was an uncured state as an intermediate substrate for preparing the composite. Fiber reinforced epoxy resin composite materials, especially carbon fiber composite material prepared by the epoxy prepreg has high specific strength and specific modulus, devisable performance and diversity of forming technology, which is widely used in construction materials, aerospace and civilian entertainment. By 2015, global composites production capacity will significantly increase, and exceed 10 million tons. However, how to deal with and recycle the waste of fiber composites have become a worldwide problem and thus prevented the fiber composite industry's growth, thereby constraining the sustainable development of fiber composites.

The recovery process of fiber composites have been reported roughly in the following ways: 1. High temperature thermal degradation (Thermochimica Acta 2007(454):109-115), which can recycle composite material to obtain clean filler and fiber, but requires high temperature processing and high standard equipment; 2. Fluidized bed (Applied surface science 2008(254): 2588-2593), which requires high temperature processing to obtain the clean fiber; 3. Supercutical fluid (water (Materials and design 2010(31):999-1002), alcohol (Ind. eng. chem. res. 2010(49):4535-4541) or carbon dioxide (CN102181071), for degrading epoxy resin system, which is still in the laboratory stage and far from practical industrialization; 4. Use of nitric acid (Journal of applied polymer science, 2004 (95): 1912-1916) to degrade the epoxy resin and obtain fiber with clean surface, which has strong corrosion resistance of acid like nitric acid, requires high standard equipment, and results in low operating security, high recycle cost, and difficult post-processing. In general, these methods have their limitations in varying degrees, existing disadvantages of fiber shortening, performance degradation, environmental pollution, and high recycling cost and so on, therefore, effective and feasible method for the recycling of waste composite materials is still an issue to be addressed in composites field.

SUMMARY OF THE INVENTION

Aiming at the problems of the existing technology, this application provides novel curing agents, methods for synthesizing these curing agents, synthetic polymer and reinforced composite materials comprising these curing agent and epoxy resin, and methods for degrading the polymer and reinforced composite materials. The prepared degradable reinforced composite materials provided by this invention have great mechanical properties and are suitable for different composite application fields; under certain conditions, the composites are degraded, and the matrix degradation products of reinforcing material and epoxy resin can be separated and recovered. Furthermore, the degradation and recovery method of reinforced composite material is economic, easy to control and can proceed in relatively mild reaction conditions.

Accordingly, in one aspect, this invention provides a curing agent for epoxy resin, having Formula I:

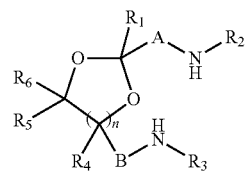

In Formula I,
each of $R_1$, $R_2$, $R_3$, $R_4$, $R_5$ and $R_6$, independently, is hydrogen, alkyl, cycloalkyl, heterocyclic, heterocycloalkyl, alkenyl, cycloalkenyl, alkynyl, aryl, heteroaryl, alkylene-oxy-alkyl, alkylene-oxy-cycloalkyl, alkylene-oxy-hetero-cyclic, alkylene-oxy-hetero-cycloalkyl, alkylene-oxy-alkenyl, alkylene-oxy-cycloalkenyl, alkylene-oxy-aryl, alkylene-oxy-heteroaryl, cycloalkylene-oxy-alkyl, cycloalkylene-oxy-cycloalkyl, cycloalkylene-oxy-heterocyclic, cycloalkylene-oxy-heterocycloalkyl, cycloalkylene-oxy-alkenyl, cycloalkylene-oxy-cycloalkenyl, cycloalkylene-oxy-aryl, cycloalkylene-oxy-heteroaryl, heterocycloalkylene-oxy-alkyl, heterocycloalkylene-oxy-cycloalkyl, heterocycloalkylene-oxy-heterocyclic, heterocycloalkylene-oxy-heterocycloalkyl, heterocycloalkylene-oxy-alkenyl, heterocycloalkylene-oxy-cycloalkenyl, heterocycloalkylene-oxy-aryl, heterocycloalkylene-oxy-heteroaryl, arylene-oxy-alkyl, arylene-oxy-cycloalkyl, arylene-oxy-heterocyclic, arylene-oxy-heterocycloalkyl, arylene-oxy-alkenyl, arylene-oxy-cycloalkenyl, arylene-oxy-aryl, or arylene-oxy-heteroaryl; and optionally $R_5$ and $R_6$, $R_1$ and A, or $R_4$ and B, together with the carbon atom(s) between $R_4$ and B, form a ring structure;
each of A and B independently is alkylene, alkylene-hetero-alkylene, alkenylene, alkenylene-hetero-alkenylene, alkylene-hetero-alkenylene, alkynylene, cycloalkylene, alkylene-cycloalkylene, alkylene-cycloalkylene-alkylene, alkenylene-cycloalkylene, alkenylene-cycloalkylene-alkenylene, alkylene-cycloalkylene-alkenylene, alkynylene-cycloalkylene, alkynylene-cycloalkylene-alkynylene, heterocycloalkylene, alkylene-heterocycloalkylene, alkylene-heterocycloalkylene-alkylene, alkenylene-heterocycloalkylene, alkenylene-heterocycloalkylene-alkenylene, alkylene-heterocycloalkylene-alkenylene, alkynylene-heterocycloalkylene, alkynylene-heterocycloalkylene-alkynylene, cycloalkenylene, alkylene-cycloalkenylene, alkylene-cycloalkenylene-alkylene, alkenylene-cycloalkenylene, alkenylene-cycloalkenylene-alkenylene, alkylene-cycloalkenylene-alkenylene, alkynylene-cycloalkenylene, alkynylene-cycloalkenylene-alkynylene, heterocycloalkenylene, alkylene-heterocycloalkenylene, alkylene-heterocycloalkenylene-alkylene, alkenylene-heterocycloalkenylene, alkenylene-heterocycloalkenylene-alkenylene, alkylene-heterocycloalkenylene-alkenylene, alkynylene-heterocycloalkenylene, alkynylene-heterocycloalkenylene-alkynylene, arylene, alkylene-arylene, alkylene-arylene-alkylene, alkenylene-arylene, alkenylene-arylene-alkenylene, alkylene-arylene-alkenylene, alkynylene-arylene, alkynylene-arylene-alkynylene, Heteroarylene, alkylene-heteroarylene, alkylene-heteroarylene-alkylene, alkenylene-heteroarylene, alkenylene-heteroarylene-alkenylene, alkylene-heteroarylene-alkenylene, alkynylene-heteroarylene, alkynylene-heteroarylene-alkynylene, carbonyl, or thiocarbonyl;

n is 1, 2, 3, or 4.

As used herein, the phrase "carbon atom(s) between [two moieties]" can refer to the carbon atom to which the two moieties both attached, or the carbon atoms that link the two moieties. For example, when n is 1, the "carbon atom(s) between [$R_4$ and B]" is the carbon atom to which both $R_4$ and B attached; when n is 2, the "carbon atom(s) between [$R_4$ and B]" are the two carbon atoms attached to $R_4$ and B, respectively; when n is 3, the "carbon atom(s) between [$R_4$ and B]" are the three carbon atoms that link $R_4$ and B, two of which are attached to $R_4$ and B, respectively; when n is 4, the "carbon atom(s) between [$R_4$ and B]" are the four carbon atoms that link $R_4$ and B.

In some embodiments, $R_1$, $R_2$, $R_3$, $R_4$, $R_5$, and $R_6$ may be the same or different; A and B may be the same or different.

In some embodiments, n is 1.

In some embodiments, each of $R_1$, $R_2$, $R_3$, $R_4$, $R_5$ and $R_6$, independently, is hydrogen or lower alkyl.

In some embodiments, each of A and B independently is alkylene, cycloalkylene, arylene, or heteroarylene.

Examples of the curing agent as described above include but are not limited to:

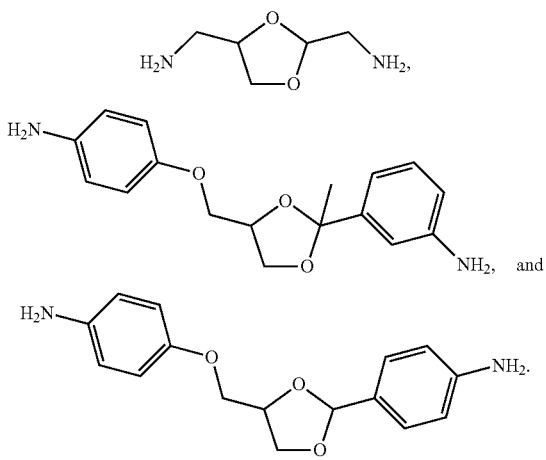

Another aspect of this invention provides methods for preparing the curing agent as described above. Set forth below are some exemplary schemes of methods that have been used or can be used for synthesizing the curing agents of this invention.

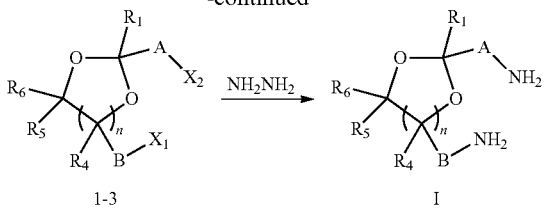

In Scheme A, each of $X_1$ and $X_2$ independently is

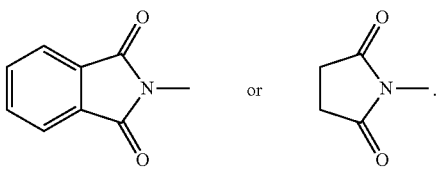

Scheme A depicts the following steps:
(1) In the presence of a catalyst, under certain conditions, Compound 1-1 reacts with Compound 1-2 in an organic solvent to give an intermediate (Compound 1-3). In some embodiments, the mole ratio of Compound 1-1 and Compound 1-2 is 0~10:1.
(2) The intermediate (Compound 1-3) undergoes an amination reaction to give a curing agent of Formula I. Formula I is defined above.

In some embodiments, in Step (1), the organic solvent is at least one selected from the group consisting of benzene, toluene, xylene, pentane, hexane, heptane, octane, nonane, cyclopentane, cyclohexane, cycloheptane, cyclooctane, tetrahydrofuran, and dioxane.

In some embodiments, in Step (1), the catalyst is at least one selected from the group consisting of p-toluenesulfonic acid, pyridinium p-toluenesulfonic acid, sulfuric acid, phosphoric acid, nitric acid, hydrogen chloride, molecular sieves, sulfonic acid resin, and solid super acid.

In some embodiments, in Step (1), the reaction temperature is 30~200° C.

In some embodiments, in Step (2), the intermediate (Compound 1-3) undergoes a hydrazine reduction to form a curing agent of Formula I. For instance, the hydrazine reduction refers to a procedure, in which intermediate (Compound 1-3) dissolves in a mixed system combined by organic solvent and hydrazine hydrate or anhydrous hydrazine, to give a curing agent of Formula I under certain reaction temperature.

In some embodiments, the organic solvent in Step (2) is at least one selected from the group consisting of benzene, toluene, xylene, pentane, hexane, heptane, octane, nonane, cyclopentane, cyclohexane, cycloheptane, cyclooctane, tetrahydrofuran, and dioxane; the reaction temperature in Step (2) is 20~150° C.

Scheme A

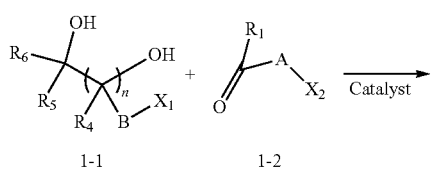

Scheme B

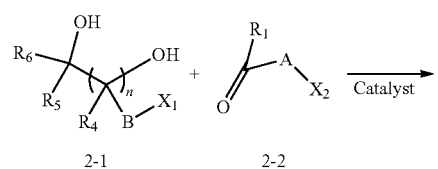

-continued

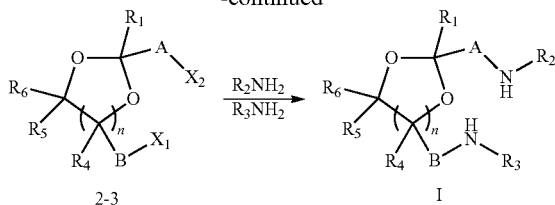

2-3    I

In Scheme B, each of $X_1$ and $X_2$ independently is chlorine, bromine, iodine, methanesulfonic acid ester, trifluoromethanesulfonate, or p-toluenesulfonic ester group.

Scheme B depicts the following steps:
(1) In the presence of a catalyst, under certain conditions, Compound 2-1 reacts with Compound 2-2 in an organic solvent to give an intermediate (Compound 2-3). In some embodiments, the mole ratio of compound 2-1 and compound 2-2 is 0~10:1.
(2) The intermediate (Compound 2-3) undergoes an amination reaction to give a curing agent of Formula I. Formula I is defined above.

In some embodiments, in Step (1), the organic solvent is at least one selected from the group consisting of benzene, toluene, xylene, pentane, hexane, heptane, octane, nonane, cyclopentane, cyclohexane, cycloheptane, cyclooctane, tetrahydrofuran, and dioxane; the catalyst is at least one selected from the group consisting of p-toluenesulfonic acid, pyridinium p-toluenesulfonic acid, sulfuric acid, phosphoric acid, nitric acid, hydrogen chloride, molecular sieves, sulfonic acid resin, and solid super acid; the reaction temperature is 30~200° C.

In some embodiments, in Step (2), the intermediate (Compound 2-3) undergoes an amination reaction to form a curing agent of Formula I. For instance, the amination reaction refers to a procedure, in which the intermediate (Compound 2-3), $R_2NH_2$ and $R_3NH_2$ dissolve in an organic solvent or in a mixed system combined by water and organic solvent, with or without a catalyst at a certain reaction temperature, to give cyclic acetal, cyclic ketal mixing polyamine reaction liquid, and after neutralization, solvent extraction and vacuum distillation, to give a curing agent of Formula I.

In some embodiments, in Step (2), the mole ratio of the intermediate (Compound 2-3) and the sum of $R_2NH_2$ and $R_3NH_2$ is 1:2~500. For example, when the amount of intermediate (Compound 2-3) is 1 mole, the amount of catalyst may be from 0 to 100 mole.

In some embodiments, in Step (2), each of $R_2NH_2$ and $R_3NH_2$ independently is liquid ammonia, ammonia, or organic amines.

In some embodiments, in Step (2), the organic solvent is at least one selected from the group consisting of benzene, toluene, xylene, pentane, hexane, heptane, octane, nonane, cyclopentane, cyclohexane, cycloheptane, cyclooctane, tetrahydrofuran, and dioxane;

In some embodiments, in Step (2), the catalyst can be ammonium carbonate, ammonium bicarbonate, ammonium acetate, hexamine, ammonium chloride, ammonium bromide, ammonium iodide, ammonium hydroxide, ammonium sulfate, ammonium bisulfate, ammonium sulfite, ammonium bisulfite, ammonium nitrate, ammonium phosphate, diammonium hydrogen phosphate, ammonium dihydrogen phosphate, ammonium formate, ammonium propionate, ammonium trifluoroacetate or ammonium benzoate.

In some embodiments, in Step (2), the reaction temperature is 10~200° C.; the reaction time can be 2~240 hours at reaction temperature.

In some embodiments, in Step (2), the neutralization reaction refers to a procedure to adjust the pH ≥7 of the reaction liquid by using aqueous alkaline solution. Examples of the alkali used in such neutralization step include, but are not limited to, lithium hydroxide, sodium hydroxide, potassium hydroxide, calcium hydroxide, sodium carbonate, sodium bicarbonate, potassium carbonate, potassium bicarbonate, and ammonia. The mass concentration of the said aqueous alkaline solution can be 0.1~100%.

In some embodiments, in Step (2), the solvent extraction refers to a procedure using an organic solvent to extract the cyclic acetal, cyclic ketal mixing polyamineis from the neutralized reaction solution. In some further embodiments, the organic solvent used in the solvent extraction step is chloroform, dichloromethane, methanol, ethanol, propanol, isopropanol, butanol, isobutanol, t-butanol, ethyl acetate, or ethyl ether.

In some embodiments, in Step (2), the vacuum fractionation refers to a procedure separating the degradable cyclic acetal, cyclic ketal diamines from the cyclic acetal, cyclic ketal mixing polyamine extract under a reduced pressure condition.

Scheme C

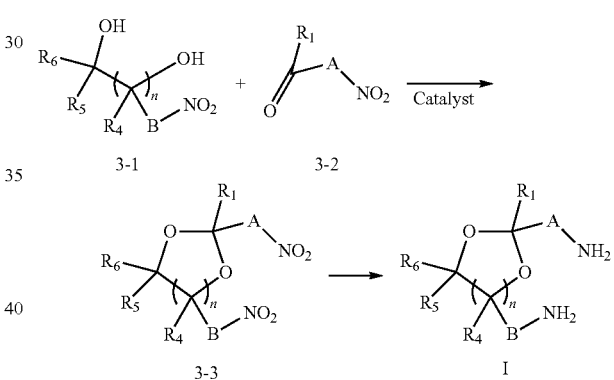

Scheme C depicts the following steps:
(1) In the presence of a catalyst, under certain conditions, Compound 3-1 reacts with Compound 3-2 to form an intermediate (Compound 3-3) in an organic solvent. In some embodiments, the mole ratio of Compound 3-1 and Compound 3-2 is 0~10:1.
(2) The intermediate (Compound 3-3) undergoes an amination reaction to form a curing agent of Formula I. Formula I is defined above.

In some embodiments, in Step (1), the organic solvent is at least one selected from the group consisting of benzene, toluene, xylene, pentane, hexane, heptane, octane, nonane, cyclopentane, cyclohexane, cycloheptane, cyclooctane, tetrahydrofuran, and dioxane; the catalyst is at least one selected from the group consisting of p-toluenesulfonic acid, pyridinium p-toluenesulfonic acid, sulfuric acid, phosphoric acid, nitric acid, hydrogen chloride, molecular sieves, sulfonic acid resin, and solid super acid; the reaction temperature is 30~200° C.

In some embodiments, in Step (2), the intermediate (Compound 3-3) undergoes a reduction reaction to form a curing agent of Formula I. In some embodiments, the reduction reaction is hydrazine reduction, catalytic hydrogenation, metal reduction, or sulfide reduction. For instance, the hydrazine reduction refers to a procedure in which the intermediate (Compound 3-3) dissolves in the mixed system combined by organic solvent and hydrazine hydrate or anhydrous hydrazine, and forms a curing agent of Formula I in the presence of catalyst.

In some embodiments, in Step (2), the organic solvent is methanol, ethanol, propanol, isopropanol, butanol, isobutanol, t-butanol, pentanol, hexanol, heptanol, octanol, nonanol, decanol, dioxane, or Ethylene glycol; the catalyst is apalladium, platinum on activated carbon, six hydrated ferric chloride, ferric chloride, iron sesquioxide, or magnesium oxide; the reaction temperature is 20~150° C.

A further aspect of this invention provides a cross-linked polymer formed by a curing agent of this invention (e.g., a curing agent of Formula I) and an epoxy resin, wherein the cross-linked polymer comprises a cross-linking group of Formula II:

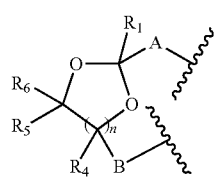

In this Formula II,
each of $R_1$, $R_4$, $R_5$ and $R_6$, independently, is hydrogen, alkyl, cycloalkyl, heterocyclic, heterocycloalkyl, alkenyl, cycloalkenyl, alkynyl, aryl, heteroaryl, alkylene-oxy-alkyl, alkylene-oxy-cycloalkyl, alkylene-oxy-hetero-cyclic, alkylene-oxy-hetero-cycloalkyl, alkylene-oxy-alkenyl, alkylene-oxy-cycloalkenyl, alkylene-oxy-aryl, alkylene-oxy-heteroaryl, cycloalkylene-oxy-alkyl, cycloalkylene-oxy-cycloalkyl, cycloalkylene-oxy-heterocyclic, cycloalkylene-oxy-heterocycloalkyl, cycloalkylene-oxy-alkenyl, cycloalkylene-oxy-cycloalkenyl, cycloalkylene-oxy-aryl, cycloalkylene-oxy-heteroaryl, heterocycloalkylene-oxy-alkyl, heterocycloalkylene-oxy-cycloalkyl, heterocycloalkylene-oxy-heterocyclic, heterocycloalkylene-oxy-heterocycloalkyl, heterocycloalkylene-oxy-alkenyl, heterocycloalkylene-oxy-cycloalkenyl, heterocycloalkylene-oxy-aryl, heterocycloalkylene-oxy-heteroaryl, arylene-oxy-alkyl, arylene-oxy-cycloalkyl, arylene-oxy-heterocyclic, arylene-oxy-heterocycloalkyl, arylene-oxy-alkenyl, arylene-oxy-cycloalkenyl, arylene-oxy-aryl, or arylene-oxy-heteroaryl; and optionally $R_5$ and $R_6$, $R_1$ and A, or $R_4$ and B, together with the carbon atom(s) between them, form a ring structure;

each of A and B independently is alkylene, alkylene-hetero-alkylene, alkenylene, alkenylene-hetero-alkenylene, alkylene-hetero-alkenylene, alkynylene, cycloalkylene, alkylene-cycloalkylene, alkylene-cycloalkylene-alkylene, alkenylene-cycloalkylene, alkenylene-cycloalkylene-alkenylene, alkylene-cycloalkylene-alkenylene, alkynylene-cycloalkylene, alkynylene-cycloalkylene-alkynylene, heterocycloalkylene, alkylene-heterocycloalkylene, alkylene-heterocycloalkylene-alkylene, alkenylene-heterocycloalkylene, alkenylene-heterocycloalkylene-alkenylene, alkylene-heterocycloalkylene-alkenylene, alkynylene-heterocycloalkylene, alkynylene-heterocycloalkylene-alkynylene, cycloalkenylene, alkylene-cycloalkenylene, alkylene-cycloalkenylene-alkylene, alkenylene-cycloalkenylene, alkenylene-cycloalkenylene-alkenylene, alkylene-cycloalkenylene-alkenylene, alkynylene-cycloalkenylene, alkynylene-cycloalkenylene-alkynylene, heterocycloalkenylene, alkylene-heterocycloalkenylene, alkylene-heterocycloalkenylene-alkylene, alkenylene-heterocycloalkenylene, alkenylene-heterocycloalkenylene-alkenylene, alkylene-heterocycloalkenylene-alkenylene, alkynylene-heterocycloalkenylene, alkynylene-heterocycloalkenylene-alkynylene, arylene, alkylene-arylene, alkylene-arylene-alkylene, alkenylene-arylene, alkenylene-arylene-alkenylene, alkylene-arylene-alkenylene, alkynylene-arylene, alkynylene-arylene-alkynylene, heteroarylene, alkylene-heteroarylene, alkylene-heteroarylene-alkylene, alkenylene-heteroarylene, alkenylene-heteroarylene-alkenylene, alkylene-heteroarylene-alkenylene, alkynylene-heteroarylene, or alkynylene-heteroarylene-alkynylene;
n is 1, 2, 3, or 4.

In some embodiments, $R_1$, $R_4$, $R_5$ and $R_6$ may be the same or different; A and B may be the same or different.

In some embodiments, n is 1.

In some embodiments, each of $R_1$, $R_4$, $R_5$ and $R_6$, independently, is hydrogen or lower alkyl.

In some embodiments, each of A and B independently is alkylene, cycloalkylene, arylene, or heteroarylene.

In some embodiments, the curing agent is

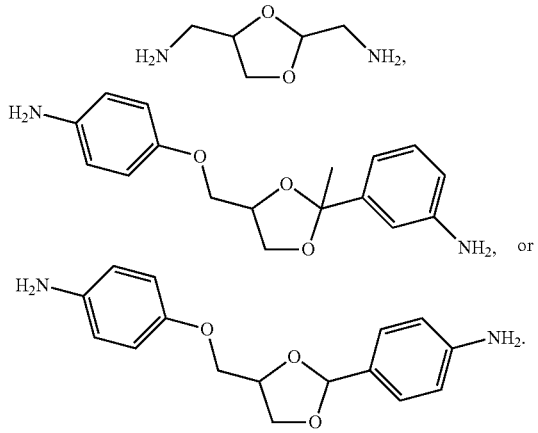

In some embodiments, the epoxy resin comprises a glycidyl ether epoxy resin, glycidyl ester epoxy resin, glycidyl amine epoxy resin, trifunctional epoxy resin, tetrafunctional epoxy resin, novolac epoxy resin, cresol-novolac epoxy resin, aliphatic epoxy resin, alicyclic epoxy resin, or nitrogen containing epoxy resin.

In some embodiments, the cross-linked polymer as described above is biodegradable.

Accordingly, another aspect of this invention provides a method for degrading the cross-linked polymer as described above.

In some embodiments, the method includes a step of degrading the cross-linked polymer as described above using a solvent and an acid (e.g., under a heating condition), and a step of neutralization using an alkali solution.

More specifically, the method may include the following steps:

(1) Under the heating and stirring conditions, the degradable cross-linked polymer is immersed in a mixed acid and solvent system for the degradation, and the degradation solution is obtained. In some embodiments, the heating temperature is 15~400° C., heating time is 1~600 hours, the mass concentration of acid in the solvent is 0.1~100%.

(2) Neutralization: using an alkaline solution at a certain temperature to control the pH of the degradation solution. In some embodiments, the temperature is 0~200° C., the final pH is more than 6, and the mass concentration of alkali solution is 0.1~100%.

In some embodiments, the acid is hydrochloric acid, hydrobromic acid, hydrofluoric acid, acetic acid, trifluoroacetic acid, lactic acid, formic acid, propionic acid, citric acid, methanesulfonic acid, p-toluenesulfonic acid, nitric acid, sulfuric acid, sulfurous acid, phosphoric acid, perchloric acid, benzoic acid, salicylic acid, or phthalic acid.

In some embodiments, the solvent is methanol, ethanol, ethylene glycol, propanol, isopropanol, butanol, isobutanol, t-butanol, pentanol, hexanol, heptanol, octanol, nonanol, benzyl alcohol, phenethyl falcohol, p-hydroxymethyl benzene, m-hydroxymethyl benzene, o-hydroxy benzene, p-hydroxyethyl benzene, m-hydroxyethyl benzene, o-hydroxyethyl benzene, water, N,N-dimethylformamide, N,N-dimethylacetamide, N-methylpyrrolidone, dimethyl sulfoxide, tetrahydrofuran, methyl tetrahydrofuran, glycerol, or dioxane.

In some embodiments, the alkali is lithium hydroxide, sodium hydroxide, potassium hydroxide, calcium hydroxide, sodium carbonate, sodium bicarbonate, potassium carbonate, potassium bicarbonate, or ammonia.

In some embodiments, the alkali solvent is methanol, ethanol, ethylene glycol, propanol, isopropanol, butanol, isobutanol, t-butanol, pentanol, hexanol, heptanol, octanol, nonanol, water, N,N-dimethylformamide, N,N-dimethylacetamide, N-methylpyrrolidone, dimethyl sulfoxide, tetrahydrofuran, methyl tetrahydrofuran, glycerol, or dioxane.

In some embodiments, in the first step, the heating temperature is 80~150° C.; heating period is 4~8 hours, the mass concentration of acid in the solvent is 0.5~20%; in the second step, the temperature is 5~50° C., the final pH is 6~12, and the concentration of alkali solution is 5~30%.

Still another aspect of this invention provides a prepreg or a reinforced composite material prepared by the curing agent of this invention. In some embodiments, the prepreg or the reinforced composite comprises a curing agent of Formula I as described above, an epoxy resin, an auxiliary material, and a reinforcing material.

In some embodiments, the epoxy resin is glycidyl ether epoxy resin, glycidyl ester epoxy resins, glycidyl epoxy amine epoxy resins, trifunctional epoxy resins, tetrafunctional epoxy resins, novolac epoxy resin, o-cresol formaldehyde epoxy resin, aliphatic epoxy resin, alicyclic epoxy resin, or nitrogen-containing epoxy resin.

In some embodiments, the reinforcing material comprises at least one of carbon nanotubes, boron nitride nanotubes, carbon black, metal nano-particles, metal oxide nanoparticles, organic nanoparticles, iron oxide, glass fibers, carbon fibers, natural fibers, synthetic fibers and the fabric made up by fiber material.

In some embodiments, the auxiliary material comprises at least one of accelerators, diluents, plasticizers, toughening agents, thickening agents, coupling agents, defoamers, flatting agent, ultraviolet absorbers, antioxidants, brighteners, fluorescent agents, pigments, and filler.

In some embodiments, the reinforced composite is degradable and recyclable.

Yet still another aspect of this invention provides a method for recycling or degrading the reinforced composite as described above.

In some embodiments, the method includes a step of degrading the reinforced composite using a solvent and an acid (e.g., under a heating condition), a step of neutralization using an alkali solution, and a step of separation (e.g., physical separation).

More specifically, the method may include the following steps:

(1) Under conditions of heating and stirring, immerse reinforced composite material in a degradation system mixed with acid and solvent, and the degradation solution is obtained. In some embodiments, the mass concentration of acid in the solvent is 0.1~100%; the heating temperature is 15~400° C., heating time is 1~600 hours.

(2) Neutralization: using an alkaline solution to adjust the pH of the degradation solution in step (1). In some embodiments, the concentration of alkali solution is 0.1~100%, the range of the temperature should be kept to adjust the pH of the degradation solution is 0~200° C., the final pH of the degradation solution is more than 6, and a precipitate was produced.

(3) Physical separation, washing and drying of the precipitate and degradation solution after pH adjusting in step (2).

In some embodiments, the acid is hydrochloric acid, hydrobromic acid, hydrofluoric acid, acetic acid, trifluoroacetic acid, lactic acid, formic acid, propionic acid, citric acid, methanesulfonic acid, p-toluenesulfonic acid, nitric acid, sulfuric acid, sulfurous acid, phosphoric acid, perchloric acid, benzoic acid, salicylic acid, or phthalic acid.

In some embodiments, the solvent is at least one of methanol, ethanol, ethylene glycol, propanol, isopropanol, butanol, isobutanol, t-butanol, pentanol, hexanol, heptanol, octanol, nonanol, benzyl alcohol, phenethyl alcohol, p-hydroxymethyl benzene, m-hydroxymethyl benzene, o-hydroxy benzene, p-hydroxyethyl benzene, m-hydroxyethyl benzene, o-hydroxyethyl benzene, water, N,N-dimethylformamide, N,N-dimethylacetamide, N-methylpyrrolidone, dimethyl sulfoxide, tetrahydrofuran, methyl tetrahydrofuran, glycerol, and dioxane.

In some embodiments, the alkali is at least one of lithium hydroxide, sodium hydroxide, potassium hydroxide, calcium hydroxide, sodium carbonate, sodium bicarbonate, potassium carbonate, potassium bicarbonate, and ammonia.

In some embodiments, the alkali solvent is at least one of methanol, ethanol, ethylene glycol, propanol, isopropanol, butanol, isobutanol, t-butanol, pentanol, hexanol, heptanol, octanol, nonanol, water, N,N-dimethylformamide, N,N-dimethylacetamide, N-methylpyrrolidone, dimethyl sulfoxide, tetrahydrofuran, methyl tetrahydrofuran, glycerol, and dioxane.

In some embodiments, in Step (1), the mass concentration of acid in the solvent is 0.5~20%; the heating temperature is 80~200° C.; and heating time is 2~12 hours.

In some embodiments, in Step (2), the mass concentration of alkali solution is 5~30%; and the temperature is 5~60° C.

In some embodiments, the reinforced composites can be made by a prepreg forming method.

This invention provides at least the following technical advantages:

(1) This invention provides composites formed by degradable epoxy resin curing agent, epoxy resin, auxiliary material and reinforcing material. Such composites can degrade under relatively mild temperature, with more than 95% of reinforcing materials can be recycled (such as carbon fiber, glass fiber, synthetic fiber and natural fiber), and can maintain most of the original texture and mechanical properties, so that they can be reused in new composites. The recycled epoxy resin polymer degradation products can be used in plastic products after processing. The epoxy resin reinforced composite with degradable property, which is generated by degradable epoxy resin curing agent, introduced by this invention has not been reported. Thus, this invention provides novel, highly efficient, feasible, and economic methods for recovering epoxy resin and reinforcing materials.

(2) According to this invention, during the degradation procedure of the epoxy resin composite, the cross-linked structure of epoxy resin matrix will have the specific chemical bonds fracture under the action of acid, resulting in the degradation of the epoxy resin matrix. Then the cross-linked structure transfers to the non-cross-linked epoxy resin polymer (like thermoplastic epoxy resin) which can dissolve in the organic solvent. When the epoxy resin matrix fully dissolves in an organic solvent, fiber reinforcing materials can be separated from the solvent. After alkali neutralization, sedimentation, and solid-liquid separation, degraded products of epoxy resin matrix are recycled. Both recycled reinforcing materials and non-cross-linked polymer can be separated, recycled and reused. By far, the reinforcing material of the thermosetting composite can only be recycled after burning out the plastic parts of the composite. Thus, this invention provides novel biodegradable epoxy resin adhesives composite, and the plastic part and reinforcing material of such composite can be recycled with high efficiency. In particular, (a) Cross-linked epoxy resin curing products can be degraded to form thermoplastic epoxy resin polymer. The degradation procedure only has limited loss of shrinkage group, and the resulted thermoplastic epoxy resin polymer has high recycling quality. Such polymer can be processed for industrial uses.

(b) The recycling quality ratio of epoxy resin curing products or reinforcing materials is more than 96%, and the recycled reinforcing materials is very stable under the acid condition. The surface of the recycled reinforcing material is clean and basically has no defect.

(c) The methods for recycling and degrading epoxy resin composites also have the following advantages: mild reaction conditions, economic, and easy to control.

As used herein, the term "alkyl," when used alone or as part of a larger moiety (e.g., as in "cycloalkenylalkyl"), refers to a saturated aliphatic hydrocarbon group. It can contain 1 to 12 (e.g., 1 to 8, 1 to 6, or 1 to 4) carbon atoms. As a moiety, it can be denoted as $—C_nH_{2n+1}$. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, and 2-ethylhexyl. An alkyl group can be substituted (i.e., optionally substituted) with one or more substituents. When an alkyl is preceded by a carbon-number modifier, e.g., $C_{1-8}$, its means the alkyl group contains 1 to 8 carbon atoms.

As used herein, the term "alkylene," when used alone or as part of a larger moiety (e.g., as in "arylaalkyleneoxy"), refers to a saturated aliphatic hydrocarbon group with two radical points for forming two covalent bonds with two other moieties. It can contain 1 to 12 (e.g., 1 to 8, 1 to 6, or 1 to 4) carbon atoms. As a moiety, it can be denoted as $—C_nH_{2n}—$. Examples of an alkylene group include, but are not limited to, methylene ($—CH_2—$), ethylene ($—CH_2CH_2—$), and propylene ($—CH_2CH_2CH_2—$). When an alkylene is preceded by a carbon-number modifier, e.g., $C_{2-8}$, its means the alkylene group contains 2 to 8 carbon atoms.

As used herein, the term "alkynyl," when used alone or as part of a larger moiety (e.g., as in "alkynylalkyl"), refers to an aliphatic hydrocarbon group with at least one triple bond. It can contain 2 to 12 (e.g., 2 to 8, 2 to 6, or 2 to 4) carbon atoms. An alkynyl group can be straight or branched. Examples of an alkynyl group include, but are not limited to, propargyl and butynyl. When an alkynyl is preceded by a carbon-number modifier, e.g., $C_{2-8}$, its means the alkynyl group contains 2 to 8 carbon atoms.

As used herein, the term "alkenyl," when used alone or as part of a larger moiety (e.g., as in "alkenylalkyl"), refers to an aliphatic hydrocarbon group with at least one double bond. It can contain 2 to 12 (e.g., 2 to 8, 2 to 6, or 2 to 4) carbon atoms. An alkenyl group with one double bond can be denoted as $—C_nH_{2n-1}$, or $—C_nH_{2n-3}$ with two double bonds. Like an alkyl group, an alkenyl group can be straight or branched. Examples of an alkenyl group include, but are not limited to, allyl, isoprenyl, 2-butenyl, and 2-hexenyl. When an alkylene is preceded by a carbon-number modifier, e.g., $C_{3-8}$, its means the alkylene group contains 3 to 8 carbon atoms.

As used herein, the term "cycloalkyl," when used alone or as part of a larger moiety (e.g., as in "cycloalkylalkyl"), refers to a saturated carbocyclic mono-, bi-, or tri-cyclic (fused or bridged or spiral) ring system. It can contain 3 to 12 (e.g., 3 to 10, or 5 to 10) carbon atoms. Examples of cycloalkyl groups include, but are not limited to, cyclopropyl, cyclobutyl, cyclopentyl, cyclohexyl, cycloheptyl, adamantyl, norbornyl, cubyl, octahydro-indenyl, decahydro-naphthyl, bicyclo[3.2.1]octyl, bicyclo[2.2.2]octyl, bicyclo[3.3.1]nonyl, bicyclo[3.3.2.]decyl, bicyclo[2.2.2]octyl, adamantyl, azacycloalkyl, or ((aminocarbonyl)cycloalkyl)cycloalkyl. When a cycloalkyl is preceded by a carbon-number modifier, e.g., $C_{3-8}$, its means the alkyl group contains 3 to 8 carbon atoms.

As used herein, the term "cycloalkenyl," when used alone or as part of a larger moiety (e.g., as in "cycloalkenylalkyl"), refers to a non-aromatic carbocyclic ring system having one or more double bonds. It can contain 3 to 12 (e.g., 3 to 10, or 5 to 10) carbon atoms. Examples of cycloalkenyl groups include, but are not limited to, cyclopentenyl, 1,4-cyclohexa-di-enyl, cycloheptenyl, cyclooctenyl, hexahydro-indenyl, octahydro-naphthyl, cyclohexenyl, cyclopentenyl, bicyclo[2.2.2]octenyl, orbicyclo[3.3.1]nonenyl.

As used herein, the term "heterocycloalkyl," when used alone or as part of a larger moiety (e.g., as in "heterocycloalkylalkyl"), refers to a 3- to 16-membered mono-, bi-, or tri-cyclic (fused or bridged or spiral)) saturated ring structure, in which one or more of the ring atoms is a heteroatom (e.g., N, O, S, or combinations thereof). In addition to the heteroatom(s), the heterocycloalkyl can contain 3 to 15 carbon atoms (e.g., 3 to 12 or 5 to 10). Examples of a heterocycloalkyl group include, but are not limited to, piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholyl, octahydrobenzofuryl, octahydrochromenyl, octahydrothiochromenyl, octahydroindolyl, octahydropyrindinyl, decahydroquinolinyl, octahydrobenzo[b]thiopheneyl, 2-oxa-bicyclo[2.2.2]octyl, 1-azabicyclo[2.2.2]octyl, 3-aza-bicyclo[3.2.1]octyl, and 2,6-dioxa-tricyclo[3.3.1.0³,⁷]nonyl. A monocyclic heterocycloalkyl group can be fused with a phenyl moiety such as tetrahydroisoquinoline. When a heterocycloalkyl is preceded by a carbon-number modifier, e.g., $C_{4-8}$, its means the heterocycloalkyl group contains 4 to 8 carbon atoms.

As used herein, the term "hetero," when used alone or as part of a larger moiety (e.g., as in "heterocyclo," "heterocycloalkyl," "heterocycloalkylene" or "heteroaryl"), refers to a hetero atom or group that is —O—, —S—, —NH—, or —C(=O)—.

As used herein, the term "aryl," when used alone or as part of a larger moiety (e.g., as in "arylkyl," or "arylkoxy"), refers to a monocyclic (e.g., phenyl), bicyclic (e.g., indenyl, naphthalenyl, or tetrahydronaphthyl), and tricyclic (e.g., fluorenyl, tetrahydrofluorenyl, tetrahydroanthracenyl, or anthracenyl) ring system in which the monocyclic ring system is aromatic (e.g., phenyl) or at least one of the rings in a bicyclic or tricyclic ring system is aromatic (e.g., phenyl). The bicyclic and tricyclic groups include, but are not limited to, benzo-fused 2- or 3-membered carbocyclic rings. For instance, a benzo-fused group includes phenyl fused with two or more $C_{4-8}$ carbocyclic moieties.

As used herein, the term "heteroaryl" refers to a monocyclic, bicyclic, or tricyclic ring system having 5 to 15 ring atoms wherein at least one of the ring atoms is a heteroatom (e.g., N, O, S, or combinations thereof) and when the monocyclic ring system is aromatic or at least one of the rings in the bicyclic or tricyclic ring systems is aromatic. It can contain 5 to 12 or 8 to 10 ring atoms. A heteroaryl group includes, but is not limited to, a benzo-fused ring system having 2 to 3 rings. For example, a benzo-fused group includes benzo fused with one or two 4- to 8-membered heterocycloalkyl moieties (e.g., indolizyl, indolyl, isoindolyl, 3H-indolyl, indolinyl, benzo[b]furyl, benzo[b]thiophenyl, quinolinyl, or isoquinolinyl). Some examples of heteroaryl are pyridyl, IH-indazolyl, furyl, pyrrolyl, thienyl, thiazolyl, oxazolyl, imidazolyl, tetrazolyl, benzofuryl, isoquinolinyl, benzithiazolyl, xanthenyl, thioxanthenyl, phenothiazinyl, dihydroindolyl, benzo[1,3]dioxolyl, benzo[b]furyl, benzo [bjthiophenyl, indazolyl, benzimidazolyl, benzthiazolyl, puryl, quinolinyl, quinazolinyl, phthalazyl, quinazolyl, quinoxalyl, isoquinolinyl, 4H-quinolizyl, benzo-1,2,5-thiadiazolyl, and 1,8-naphthyridyl.

As used herein, the suffix "-ene" is used to describe a bivalent group with two radical points for forming two covalent bonds with two other moieties. In other words, any of the terms as defined above can be modified with the suffix "-ene" to describe a bivalent version of that moiety. For example, a bivalent aryl ring structure is "arylene," a bivalent benzene ring structure is "phenylene," a bivalent heteroaryl ring structure is "heteroarylene," a bivalent cycloalkyl ring structure is a "cycloalkylene," a bivalent heterocycloalkyl ring structure is "heterocycloalkylene," a bivalent cycloalkenyl ring structure is "cycloalkenylene," a bivalent alkenyl chain is "alkenylene," and a bivalent alkynyl chain is "alkynylene."

As used herein, the term "optionally" (e.g., as in "optionally substituted with") means that the moiety at issue is either substituted or not substituted, and that the substitution occurs only when chemically feasible. For instance, H cannot be substituted with a substituent and a covalent bond or —C(=O)— group cannot be substituted with a substituent.

As used herein, an "oxo" group refers to =O.

As used herein, a "carbonyl" group refers to —C(O)— or —C(=O)—.

As used herein, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different in every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

For convenience and as commonly understood, the term "optionally substituted" only applies to the chemical entities that can be substituted with suitable substituents, not to those that cannot be substituted chemically.

As used herein, the term "or" can mean "or" or "and."

DETAILED DESCRIPTION OF THE INVENTION

The following examples are provided for illustration only, and not intended to be limiting in any aspect.

EXAMPLE 1

Preparation of Curing Agent 1

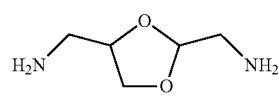

1

Method 1:

189 g N-(2-Oxoethyl)phthalimide, 221 g 2-(2,3-dihydroxypropyl)isoindole-1,3-dione, 5 g anhydrous p-toluene sulfonic acid and 1 L toluene were mixed at room temperature, then the solution was heated to reflux with DEAN-STARK apparatus to distill the evolved water. After 20 hours, the reaction was completed. The solution was cooled to room temperature, 2 L petroleum ether (bp: 60-90° C.) was added, filtered, the solid was washed with 1 L petroleum ether (bp: 60-90° C.) and dried to give 950 g crude. Then 3.4 L 20% aq. NaOH was added and the solution was heated to reflux, after 10 hours at reflux, cooled, extracted with chloroform/isopropyl alcohol, separated, the organic phase was dried with anhydrous sodium sulfate, then distilled at reduced pressure to give 80 g Curing Agent 1.

Method 2:

800 g methylbenzene and 440 g 3-Chloro-1,2-propanediol were placed in the reaction bottle, 548 g dimethylchloroacetal and 3 g p-toluenesulfonic acid were added under stirring. The solution was slowly heated to reflux with Dean-Stark apparatus to distil evolved methanol. After 12-16 hours, the reaction was completed, and the solution was cooled to below 40° C., a moderate amount of sodium carbonate was added into the reaction bottle, the solution was neutralized to pH close to 7. The reaction solution was concentrated at reduced pressure; toluene was recycled to give 760 g chlorinated intermediate.

400 mL N,N-dimethylformamide was placed into the three flask, while stirring 231 g potassium phthalimide and 86.5 g chlorinated intermediate were added. The solution was heated to 150° C., after 8 hours (the reaction was completed), concentrated at reduced pressure and DMF was recycled. The residue could be used for the next step without purification. 320 g NaOH and 960 g water were added into the residue at room temperature, then the solution was heated to reflux, after reflux for 12 hours, cooled to room temperature, extracted with chloroform/ethanol (Volume ratio 3:1) for 3 times. The organic phase was combined and dried with anhydrous sodium sulfate, filtered, concentrated at reduced pressure, then distilled at reduced pressure to give 50 g Curing Agent 1.

Method 3:

300 g liquid ammonia was placed into the high pressure reactor and 30 g intermediate of method 2 was added while stirring at room temperature, then the solution was slowly heated to 90° C. After 6 hours, the reaction was completed by TLC monitoring. Most of solvent were concentrated at reduced the pressure, then the residue was transferred to the reaction bottle, 30% aq. NaOH was added and the residue was neutralized to pH≥10, then extracted with 100 mL chloroform/ethanol (volume ratio 3:1) for 3 times, the organic phase was combined and dried with anhydrous sodium sulfate or anhydrous magnesium sulfate, filtered, the filter cake was washed with small amount of solvent, then the filtrate was concentrated and distilled at reduced pressure to give 15 g Curing Agent 1.

LC/MS (M+1): 133.

$^1$H-NMR (CDCl$_3$, 400 MHz): 5.13 (t, 1H), 4.13 (m, 1H), 3.73 (d, 2H), 2.90 (d, 2H), 2.83 (d, 2H)

EXAMPLE 2

Preparation of Curing Agent 2

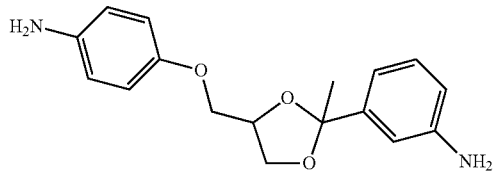

Step (1)

221 g sodium hydroxide was dissolved in 1.5 L ethyl alcohol, the solution was added in a 5 L stirring reactor while the temperature was controlled below 40° C. Then 700 g 4-Nitrophenol and 3 L ethanol were added and, during the procedure, the precipitate was formed. After 2 hours at 40° C., the reaction solution was concentrated to give sodium 4-nitrophenoxide.

Step (2)

800 g toluene and 480 g 3-chloro-1,2-propanediol were placed into the reaction flask, while stirring, 660 g nitroacetophenone and 1.5 g p-toluenesulfonic acid were added, the reaction solution was slowly heated to reflux with Dean-Stark trap to distil the water. After the reaction was completed by TLC monitoring, the solution was cooled to below 40° C., moderate amount of sodium carbonate was added into the reaction flask, the reaction solution was neutralized to pH close to 7, concentrated at reduced the pressure, most of the toluene was recycled, hot water was added to crystallize, filtered, dried to give 1100 g crude solid.

Step (3)

The crude solid prepared by the above step can be used without further purification. In a 1 L three round bottom flask, while stirring, 400 mL N,N-dimethylformamide (DMF) and 180 g sodium 4-nitrophenoxide prepared by Step (1) and 260 g crude solid prepared by Step (2) were added, the reaction solution was heated to 120~130° C. After the reaction was completed by TLC monitoring, DMF was recycled at reduced pressure, after the residue was cooled, water was added till yellow precipitate was appeared, filtered, the solid was dried at vacuum to give 325 g yellow solid.

Step (4)

In a 2 L three round bottom flask, the yellow solid prepared by Step (3) dissolved in 1.3 L tetrahydrofuran, 8.2 g 10% Pd/C and 200 g 80% hydrazine hydrate were added. The reaction solution was heated to reflux. After the reaction was completed by TLC monitoring, the solution was cooled, filtered, and 10% Pd/C was recycled. Mother solution was evaporated by rotary evaporator, and the residue was recrystallized with petroleum ether/ethyl acetate to give 230 g Curing Agent 2.

LC/MS (M+1): 301.

1H-NMR (CDCl3, 400 MHz): 7.13 (t, 1H), 6.74 (d, 2H), 6.72 (d, 1H), 6.68 (s, 1H), 6.66 (d, 2H), 6.56 (d, 1H), 4.40 (m, 1H), 4.08 (d, 2H), 3.86 (d, 2H), 1.74 (s, 3H)

EXAMPLE 3

Preparation of Curing Agent 3

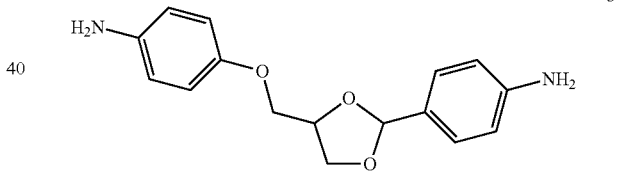

Step (1)

800 g toluene and 440 g 3-Chloro-1,2-propanediol were placed into the reaction flask, then while stirring 660 g nitroacetophenone and 3 g p-toluenesulfonic acid were added. The reaction solution was slowly heated to reflux with Dean-Stark trap to distil the water. After the reaction was completed by TLC monitoring, the solution was cooled to below 40° C., moderate amount of sodium carbonate was added into the reaction flask, the reaction solution was neutralized to pH close to 7, concentrated at reduced pressure, most of toluene was recycled, hot water was added till precipitate was prepared, filtered, dried to give 1000 g crude solid.

Step (2)

The crude solid prepared by the above step can be used without further purification. In a 1 L three round bottom flask, while stirring, 400 mL N,N-dimethylformamide (DMF), 180 g sodium 4-nitrophenoxide, and 244 g crude solid prepared by step (1) were added, the reaction solution was heated to 120~130° C. After the reaction was completed by TLC monitoring, the solution was concentrated at vacuum and DMF was recycled. After the residue was cooled, water was added till yellow solid was appeared, filtered, the solid was dried at vacuum to give 315 g yellow solid.

Step (3)

In a 2 L three round bottom flask, the yellow solid prepared by step (2) dissolved in 1.26 L tetrahydrofuran, then 7.8 g 10% Pd/C and 250 g 80% hydrazine hydrate were added, the reaction solution was heated to reflux. After the reaction was completed by TLC monitoring, the solution was cooled, filtered and 10% Pd/C was recycled, mother solution was evaporated by rotary evaporator, and the residue was recrystallized with petroleum ether/ethyl acetate to give 220 g Curing Agent 3.

LC/MS (M+1): 287.

$^1$H-NMR (CDCl$_3$, 400 MHz): 7.11 (d, 2H), 6.74 (d, 2H), 6.66 (d, 2H), 6.56 (d, 2H), 5.79 (s, 1H), 4.40 (m, 1H), 4.08 (d, 2H), 3.86 (d, 2H)

EXAMPLE 4

Degradable Cross-linked Polymer Polymerized by the Curing Agent and Epoxy Resin 10 g Curing Agent 1 in Example 1 (AEW≈3.03 N—H eq./100 g) and 57.1 g liquid bisphenol A type epoxy resin E52D (EEW 0.52~0.54 eq./100 g) were mixed and stirred evenly at room temperature. As tested, gel time was longer than 4 hours at 70° C. The mixture could be stored for more than one month at room temperature. Appropriate amount of the mixture sample was painted on a glass slide, the reaction was heated to 120° C. for 2 hours, then to 160° C. for 2 hours until fully cured, and then then was prepared to the sample of cured degradable epoxy resin.

EXAMPLE 5

Degradable Cross-linked Polymer Polymerized by the Curing Agent and Epoxy Resin 10 g Curing Agent 2 in Example 2 (AEW≈1.33 N—H eq./100 g) and 25.1 g liquid bisphenol A type epoxy resin E52D (EEW 0.52~0.54 eq./100 g) were mixed and stirred evenly at room temperature. As tested, gel time was longer than 4 hours at 70° C. The mixture could be stored for more than one month at room temperature. An appropriate amount of the mixture was painted on a glass slide, heated to 120° C. for 2 hours, then to 160° C. for 2 hours until fully cured, and then was prepared to the sample of cured degradable epoxy resin.

EXAMPLE 6

Degradable Cross-linked Polymer Polymerized by the Curing Agent and Epoxy Resin 10 g Curing Agent 3 in Example 3 (AEW≈1.40 N—H eq./100 g) and 24.8 g liquid bisphenol F type epoxy resin (EEW 0.5~0.63 eq./100 g) were mixed and stirred evenly at room temperature. As tested, gel time was longer than 4 hours at 70° C. The mixture could be stored for more than one month at room temperature. Appropriate amount of the mixture was painted on a glass slide, heated to 70° C. for 2 hours, then to 125° C. for 2 hours until fully cured, and then was prepared to the sample of cured degradable epoxy resin.

EXAMPLE 7

Degradation and Recycling of Degradable Cross-linked Polymer 0.5 g cured sample in Example 4, 10 mL concentrated hydrochloric acid and 90 mL ethylene glycol were placed in a one-neck round flask, stirred and heated to 180° C., completely degraded after 10 hours to give transparent clear solution, which was neutralized with 20% sodium hydroxide solution. Precipitated solid was filtered and the solid was washed with water and dried to give 0.49 g of degradation products of thermoset epoxy resin, mass recovery ratio was 95%.

EXAMPLE 8

Degradation and Recycling of Degradable Cross-linked Polymer 0.6 g cured sample in Example 4, 0.1 mL concentrated hydrochloric acid, and 90 mL ethylene glycol were placed in an autoclave, stirred and heated to 350° C., completely degraded after 0.5 hours to give transparent clear solution, which was neutralized with 20% sodium hydroxide solution. Precipitated solid was filtered and the solid was washed with water and dried to give 0.57 g of degradation products of thermoset epoxy resin, mass recovery ratio was 95%.

EXAMPLE 9

Degradation and Recycling of Degradable Cross-linked Polymer 0.06 g cured sample in Example 4, 90 mL concentrated hydrochloric acid, and 10 mL ethylene glycol were placed in a one-neck round flask, stirred and heated to 20° C., completely degraded after 120 hours to give transparent clear solution, which was neutralized with 95% sodium hydroxide solution. Precipitated solid was filtered and the solid was washed with water and dried to give 0.059 g of degradation products of thermoset epoxy resin, mass recovery ratio was 95%.

EXAMPLE 10

Degradation and Recycling of Degradable Cross-linked Polymer 0.7 g cured sample in Example 5, 10 mL concentrated hydrochloric acid, and 90 mL ethylene glycol were placed in a one-neck round flask, stirred and heated to 190° C., completely degraded after 6 hours to give transparent clear solution, which was neutralized with 95% sodium hydroxide solution. Precipitated solid was filtered and the solid was washed with water and dried to give 0.67 g of degradation products of thermoset epoxy resin, mass recovery ratio was 95%.

EXAMPLE 11

Degradation and Recycling of Degradable Cross-linked Polymer 0.61 g of the samples of cured sample in Example 5, 10 mL concentrated hydrochloric acid and 90 mL ethylene glycol were placed in a one-neck round flask, stirred and heated to 190° C., completely degraded after 6 hours and transparent clear solution was obtained, which was neutralized with 2% sodium hydroxide solution and precipitated solid was filtered and the solid was washed with water and dried to give 0.58 g of degradation products of thermoset epoxy resin, mass recovery ratio was 95%.

EXAMPLE 12

Degradation and Recycling of Degradable Cross-linked Polymer 0.65 g cured sample in Example 5, 10 mL concentrated hydrochloric acid, and 90 mL octanol were placed in a one-neck round flask, stirred and heated to 155° C., completely degraded after 4 hours to give transparent clear solution, which was neutralized with 10% sodium hydroxide solution, and precipitated solid was filtered and the solid was washed with water and dried to give 0.62 g of degradation products of thermoset epoxy resin, mass recovery ratio was 96%.

EXAMPLE 13

Degradation and Recycling of Degradable Cross-linked Polymer 0.75 g cured sample in Example 6, 10 mL concentrated hydrochloric acid, and 90 mL hexanol were placed in a one-neck round flask, stirred and heated to 155° C., completely degraded after 4 hours and to give transparent clear solution, which was neutralized with 20% sodium hydroxide solution, and precipitated solid was filtered and the solid was washed with water and dried to give 0.71 g of degradation products of thermoset epoxy resin, mass recovery ratio was 95%.

EXAMPLE 14

Degradation and Recycling of Degradable Cross-linked Polymer 0.9 g cured sample in Example 6, 5 ml methanesulfonic acid, and 90 mL ethylene glycol were placed in a one-neck round flask, stirred and heated to 135° C., completely degraded after 6 hours and transparent to give clear solution, which was neutralized with 0.1% sodium hydroxide solution, and precipitated solid was filtered and the solid was washed with water and dried to give 0.88 g of degradation products of thermoset epoxy resin, mass recovery ratio was 98%.

EXAMPLE 15

Degradation and Recycling of Degradable Cross-linked Polymer 0.95 g cured sample in Example 6, 5 ml methanesulfonic acid, and 90 mL octanol were placed in a one-neck round flask, stirred and heated to 135° C., completely degraded after 6 hours to give transparent clear solution, which was neutralized with 90% sodium hydroxide solution, and precipitated solid was filtered and the solid was washed with water and dried to give 0.91 g of degradation products of thermoset epoxy resin, mass recovery ratio was 96%.

EXAMPLE 16

Gel Time and Shelf Time of Degradable Epoxy Resin Matrix

Bisphenol A epoxy resin E51 (EEW 0.48~0.54 eq./100 g), E20 (EEW 0.18~0.22 eq./100 g), and E44 (EEW 0.41~0.47 eq./100 g) were mixed and stirred evenly in the mass ratio (3.5:5:1.5) at 100° C. The mixture is cooled to 70° C., the equivalent amount of Curing Agent 2 in Example 2 (AEW≈1.33 N—H eq./100 g) was added, then the resin mixture was stirred at high speed. At 70° C., gel time was longer than 6 hours.

The viscosity of the resin mixture is 18000-24000 cps at 70° C. Similarly, after the resin mixture was stored at −18° C. for 7 days and 30 days, the viscosity and gel time of the resin mixture at 70° C. had no significant change; after the resin mixture was stored at 25° C. for 7 days and 30 days, the viscosity and gel time at of the resin mixture at 70° C. had no significant change.

EXAMPLE 17

Gel Time and Shelf Time of Degradable Epoxy Resin Matrix

Bisphenol A epoxy resin E52D (EEW 0.52~0.54 eq./100 g), E20 (EEW 0.18~0.22 eq./100 g), and E44 (EEW 0.41~0.47 eq./100 g) in the mass ratio (3.5:5:1.5) were mixed and stirred well at 100° C., and then cooled to 70° C., the equivalent amount of Curing Agent 3 in Example 3 (AEW≈1.40 N—H eq./100 g) was added, then the resin mixture was stirred at high speed. At 70° C., gel time of the resin mixture was longer than 6 hours.

The viscosity of the resin mixture is 18000-25000 cps at 70° C. Similarly, after the resin mixture was stored at −18° C. for 7 days and 30 days, the viscosity and gel time of the resin mixture at 70° C. had no significant change; after the resin mixture was stored at 25° C. for 7 days and 30 days, the viscosity and gel time of the resin mixture at 70° C. had no significant change.

EXAMPLE 18

Preparation of Degradable Epoxy Resin Carbon Fiber Prepreg and Carbon Fiber Composite Laminate Step 1: Preparation of Degradable Epoxy Resin Matrix 20 g bisphenol A epoxy resin E51 (EEW 0.48~0.54 eq./100 g), 25.8 g Curing Agent 2 in Example 2 (AEW≈1.33 N—H eq./100 g) were weighed and mixed in the blender, then grinded in three-roll mill for 30 minutes as standby. 15 g bisphenol A epoxy resin E51 (EEW 0.48~0.54 eq./100 g), 15 g bisphenol A epoxy resin E44 (EEW 0.41~0.47 eq./100 g), and 50 g bisphenol A epoxy resin E20 (EEW 0.18~0.22 eq./100 g) were placed into the oven, and preheat for 3 hours at 120° C., then the heated resin was put into the kneader to knead for 1 hour, cooled to 70° C., then the resin was put into the mixing blender, vacurated, former standby E51/Curing Agent 2 mixed system which had been grinded in the three-roll grinder was added at 70° C., then the resin mixture was stirred at high speed for 30 minutes, discharged, and cooled to room temperature, then frozen in store.

The gel time of the prepared degradable epoxy resin matrix as prepared above was longer than 4 hours at 70° C.

It can be stored longer than one month at room temperature, half a year at 0° C., or one year at −18° C.

Step 2: Preparation of Degradable Epoxy Carbon Fiber Prepreq and Carbon Fiber Composite Laminate The epoxy system prepared by the above step was heated to 70° C., and carbon fiber prepreg was made using 3K carbon fiber cloth by wet method. The prepregs were slightly tacky at room temperature and pressed on the tablet pressing machine at 150° C. to give laminate of carbon fiber composite.

EXAMPLE 19

Preparation of the Degradable Epoxy Resin Uni-directional Carbon Fiber Prepreg and Carbon Fiber Composite Laminate Step 1: Preparation of Biodegradable Epoxy Resin Matrix 20 g bisphenol A epoxy resin E52D (EEW 0.52~0.54 eq./100 g), 24.6 g Curing Agent 3 in Example 3 (AEW≈1.40 N—H eq./100 g) were weighed and mixed in the blender, then grinded in three-roll mill for 30 minutes as standby. 15 g bisphenol A epoxy resin E52D (EEW 0.52~0.54 eq./100 g), 15 g bisphenol A epoxy resin E44 (EEW 0.41~0.47 eq./100 g), and 50 g bisphenol A epoxy resin E20 (EEW 0.18~0.22 eq./100 g) were placed into the oven, and preheated for 3 hours at 120° C., then the heated resin was put into the kneader to knead for 1 hour, cooled 70° C., then the resin was put into the mixing blender, then vacurated, former standby E52/Curing Agent 3 mixed system, which has been grinded in the three-roll mill was added at 70° C., then the resin mixture was stirred at high speed for 30 minutes, discharged, cooled to room temperature, then frozen in store.

The gel time of the above degradable epoxy resin matrix is longer than 4 hours at 70° C. It can be stored longer than one month at room temperature, half a year at 0° C., or one year at −18° C.

Step 2: Preparation of Degradable Epoxy Carbon Fiber Prepreq and Carbon Fiber Composite Laminate The above prepared epoxy system was heated to 70° C., and carbon fiber prepreg was made using 3K carbon fiber cloth by wet method. The prepregs were slightly tacky at room temperature and pressed on the tablet pressing machine at 150° C. to give laminate of carbon fiber composite.

EXAMPLE 20

Degradation of Carbon Fiber Composite Laminate 1.5 g of the samples of the carbon fiber composite laminate in Example 18, 10 mL concentrated hydrochloric acid and 90 mL phenylcarbinol were placed in a one-neck round flask, stirred and heated to 190° C., epoxy resin matrix was completely degraded after 3 hours, filtered when the solution was hot, the carbon fiber and the degradation solution were separated, the solution was neutralized with 20% sodium hydroxide solution and precipitated solid was filtered and the solid was washed with water and dried to give 1.47 g of degradation products of thermoset epoxy resin and carbon fiber, mass recovery ratio was 98%. The surface of recycled fiber was clean and basically has no defect.

EXAMPLE 21

Degradation of Carbon Fiber Composite Laminate 1.5 g of the samples of the carbon fiber composite laminate in Example 18, 10 mL concentrated hydrochloric acid and 90 mL ethylene glycol were placed in a one-neck round flask, stirred and heated to 160° C., epoxy resin matrix was completely degraded after 3 hours, filtered when the solution was hot, the carbon fiber and the degradation solution were separated, the solution was neutralized with 30% sodium hydroxide solution and precipitated solid was filtered and the solid was washed with water and dried to give 1.46 g of degradation products of thermoset epoxy resin and carbon fiber, mass recovery ratio was 97%. The surface of recycled fiber was clean and basically has no defect.

EXAMPLE 22

Degradation of Carbon Fiber Composite Laminate 1.5 g of the samples of the carbon fiber composite laminate in Example 18, 10 mL concentrated hydrochloric acid and 90 mL hexanol were placed in a one-neck round flask, stirred and heated to 135° C., epoxy resin matrix was completely degraded after 4 hours, filtered when the solution was hot, the carbon fiber and the degradation solution were separated, the solution was neutralized with 20% sodium hydroxide solution and precipitated solid was filtered and the solid was washed with water and dried to give 1.43 g of degradation products of thermoset epoxy resin and carbon fiber, mass recovery ratio was 95%. The surface of recycled fiber was clean and basically has no defect.

EXAMPLE 23

Degradation of Carbon Fiber Composite Laminate 1.5 g of the samples of the carbon fiber composite laminate in Example 18, 10 mL concentrated hydrochloric acid and 90 mL octanol were placed in a one-neck round flask, stirred and heated to 135° C., epoxy resin matrix was completely degraded after 4 hours, filtered when the solution was hot, the carbon fiber and the degradation solution were separated, the solution was neutralized with 40% sodium hydroxide solution and precipitated solid was filtered and the solid was washed with water and dried to give 1.44 g of degradation products of thermoset epoxy resin and carbon fiber, mass recovery ratio was 96%. The surface of recycled fiber was clean and basically has no defect.

EXAMPLE 24

Degradation of Carbon Fiber Composite Laminate 1.5 g of the samples of the carbon fiber composite laminate in Example 19, 10 mL concentrated hydrochloric acid and 90 mL ethylene glycol were placed in a one-neck round flask, stirred and heated to 135° C., epoxy resin matrix was completely degraded after 4 hours, filtered when the solution was hot, the carbon fiber and the degradation solution were separated, the solution was neutralized with 20% sodium hydroxide solution and precipitated solid was filtered and the solid was washed with water and dried to give 1.42 g of degradation products of thermoset epoxy resin and carbon fiber, mass recovery ratio was 95%. The surface of recycled fiber was clean and basically has no defect.

EXAMPLE 25

Degradation of Carbon Fiber Composite Laminate 1.5 g of the samples of the carbon fiber composite laminate in Example 19, 5 ml methylsulfonic acid and 90 mL ethylene glycol were placed in a one-neck round flask, stirred and heated to 190° C., epoxy resin matrix was completely degraded after 3 hours, filtered when the solution was hot, the carbon fiber and the degradation solution were separated, the solution was neutralized with 10% sodium hydroxide solution and precipitated solid was filtered and the solid was washed with water and dried to give 1.43 g of degradation products of thermoset epoxy resin and carbon fiber, mass recovery ratio was 95%. The surface of recycled fiber was clean and basically has no defect.

EXAMPLE 26

Degradation of Carbon Fiber Composite Laminate 2 g of the samples of the carbon fiber composite laminate in Example 19, 5 ml methylsulfonic acid and 90 mL octanol were placed in a one-neck round flask, stirred and heated to 160° C., epoxy resin matrix was completely degraded after 3 hours, filtered when the solution was hot, the carbon fiber and the degradation solution were separated, the solution was neutralized with 50% sodium hydroxide solution and precipitated solid was filtered and the solid was washed with water and dried to give 1.94 g of degradation products of thermoset epoxy resin and carbon fiber, mass recovery ratio was 97%. The surface of recycled fiber was clean and basically has no defect.

EXAMPLE 27

Degradation of Carbon Fiber Composite Laminate 2 g of the samples of the carbon fiber composite laminate in Example 19, 5 ml methylsulfonic acid and 90 mL hexanol were placed in a one-neck round flask, stirred and heated to 135° C., epoxy resin matrix was completely degraded after 4 hours, filtered when the solution was hot, the carbon fiber and the degradation solution were separated, the solution was neutralized with 20% sodium hydroxide solution and precipitated solid was filtered and the solid was washed with water and dried to give 0.95 g of degradation products of thermoset epoxy resin and carbon fiber, mass recovery ratio was 1.9%. The surface of recycled fiber was clean and basically has no defect.

EXAMPLE 28

Degradation of Carbon Fiber Composite Laminate 0.5 g of the samples of the carbon fiber composite laminate in Example 19, 0.1 mL concentrated hydrochloric acid and 90 mL ethylene glycol were placed in an autoclave, stirred and heated to 350° C., epoxy resin matrix was completely degraded after 0.5 hours, cool down to 100° C., filtered when the solution was not cooled down, the carbon fiber and the degradation solution were separated, the solution was neutralized with 0.1% sodium hydroxide solution and precipitated solid was filtered and the solid was washed with water and dried to give 0.47 g of degradation products of thermoset epoxy resin and carbon fiber, mass recovery ratio was 95%.

EXAMPLE 29

Degradation of Carbon Fiber Composite Laminate 0.15 g of the samples of the carbon fiber composite laminate in Example 19, 90 ml concentrated hydrochloric acid and 2 ml ethylene glycol were placed in an autoclave, stirred and heated to 20° C., epoxy resin matrix was completely degraded after 120 hours, cool down to 100° C., filtered when the solution was not cooled down, the carbon fiber and the degradation solution were separated, the solution was neutralized with 100% sodium hydroxide solution and precipitated solid was filtered and the solid was washed with water and dried to give 0.143 g of degradation products of thermoset epoxy resin and carbon fiber, mass recovery ratio was 95%.

What is claimed is:
1. A curing agent for epoxy resin, having Formula I:

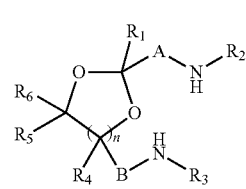

wherein:
each of $R_1$, $R_2$, $R_3$, $R_4$, $R_5$ and $R_6$, independently, is hydrogen, alkyl, cycloalkyl, heterocyclic, heterocycloalkyl, alkenyl, cycloalkenyl, alkynyl, aryl, heteroaryl, alkylene-oxy-alkyl, alkylene-oxy-cycloalkyl, alkylene-oxy-hetero-cyclic, alkylene-oxy-hetero-cycloalkyl, alkylene-oxy-alkenyl, alkylene-oxy-cycloalkenyl, alkylene-oxy-aryl, alkylene-oxy-heteroaryl, cycloalkylene-oxy-alkyl, cycloalkylene-oxy-cycloalkyl, cycloalkylene-oxy-heterocyclic, cycloalkylene-oxy-heterocycloalkyl, cycloalkylene-oxy-alkenyl, cycloalkylene-oxy-cycloalkenyl, cycloalkylene-oxy-aryl, cycloalkylene-oxy-heteroaryl, heterocycloalkylene-oxy-alkyl, heterocycloalkylene-oxy-cycloalkyl, heterocycloalkylene-oxy-heterocyclic, heterocycloalkylene-oxy-heterocycloalkyl, heterocycloalkylene-oxy-alkenyl, heterocycloalkylene-oxy-cycloalkenyl, heterocycloalkylene-oxy-aryl, heterocycloalkylene-oxy-heteroaryl, arylene-oxy-alkyl, arylene-oxy-cycloalkyl, arylene-oxy-heterocyclic, arylene-oxy-heterocycloalkyl, arylene-oxy-alkenyl, arylene-oxy-cycloalkenyl, arylene-oxy-aryl, or arylene-oxy-heteroaryl;
each of A and B independently is alkylene, alkylene-hetero-alkylene, alkenylene, alkenylene-hetero-alkenylene, alkylene-hetero-alkenylene, alkynylene, cycloalkylene, alkylene-cycloalkylene, alkylene-cycloalkylene-alkylene, alkenylene-cycloalkylene, alkenylene-cycloalkylene-alkenylene, alkylene-cycloalkylene-alkenylene, alkynylene-cycloalkylene, alkynylene-cycloalkylene-alkynylene, heterocycloalkylene, alkylene-heterocycloalkylene, alkylene-heterocycloalkylene-alkylene, alkenylene-heterocycloalkylene, alkenylene-heterocycloalkylene-alkenylene, alkylene-heterocycloalkylene-alkenylene, alkynylene-heterocycloalkylene, alkynylene-heterocycloalkylene-alkynylene, cycloalkenylene, alkylene-cycloalkenylene, alkylene-cycloalkenylene-alkylene, alkenylene-cycloalkenylene, alkenylene-cycloalkenylene-alkenylene,alkylene-cycloalkenylene-alkenylene, alkynylene-cycloalkenylene, alkynylene-cycloalkenylene-alkynylene, heterocycloalkenylene, alkylene-heterocycloalkenylene, alkylene-heterocycloalkenylene-alkylene, alkenylene-heterocycloalkenylene, alkenylene-heterocycloalkenylene-alkenylene, alkylene-heterocycloalkenylene-alkenylene, alkynylene-heterocycloalkenylene, alkynylene-heterocycloalkenylene-alkynylene, arylene, alkylene-arylene, alkylene-arylene-alkylene, alkenylene-arylene, alkenylene-arylene-alkenylene, alkylene-arylene-alkenylene, alkynylene-arylene, alkynylene-arylene-alkynylene, Heteroarylene, alkylene-heteroarylene, alkylene-heteroarylene-alkylene, alkenylene-heteroarylene, alkenylene-heteroarylene-alkenylene, alkylene-heteroarylene-alkenylene, alkynylene-heteroarylene, alkynylene-heteroarylene-alkynylene, carbonyl, or thiocarbonyl; n is 1, 2, 3, or 4 ring carbon atoms.

2. The curing agent of claim 1, wherein $R_1$, $R_2$, $R_3$, $R_4$, $R_5$ and $R_6$ are the same or different; A and B are the same or different.

3. The curing agent of claim 1, wherein n is 1.

4. The curing agent of claim 3, wherein each of $R_1$, $R_2$, $R_3$, $R_4$, $R_5$ and $R_6$, independently, is hydrogen or lower alkyl.

5. The curing agent of claim 4, wherein each of A and B independently is alkylene, cycloalkylene, arylene, or heteroarylene.

6. The curing agent of claim 1, wherein the curing agent is

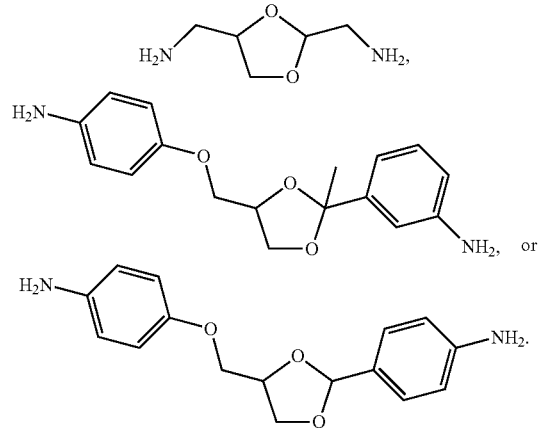

7. A method for preparing a curing agent of claim 1, comprising the steps as depicted in the following scheme:

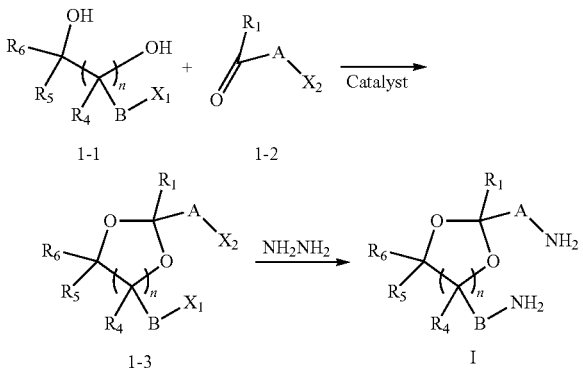

wherein each of $X_1$ and $X_2$ independently is

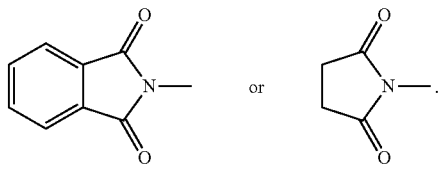

8. The method of claim 7, wherein the catalyst comprises p-toluenesulfonic acid, pyridinium p-toluenesulfonic acid, sulfuric acid, phosphoric acid, nitric acid, hydrogen chloride, molecular sieves, sulfonic acid resin, or solid super acid.

9. A method for preparing a curing agent of claim 1, comprising the steps as depicted in the following scheme:

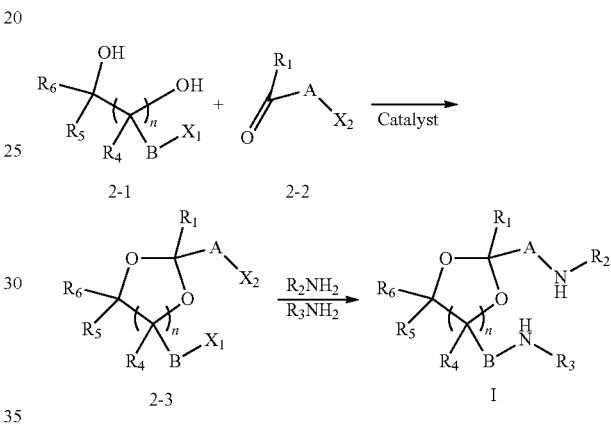

wherein each of $X_1$ and $X_2$ independently is chlorine, bromine, iodine, methanesulfonic acid ester, trifluoromethanesulfonate, or p-toluenesulfonic ester group.

10. The method of claim 9, wherein the catalyst comprises p-toluenesulfonic acid, pyridinium p-toluenesulfonic acid, sulfuric acid, phosphoric acid, nitric acid, hydrogen chloride, molecular sieves, sulfonic acid resin, or solid super acid.

11. A method for preparing a curing agent of claim 1, comprising the steps as depicted in the following scheme:

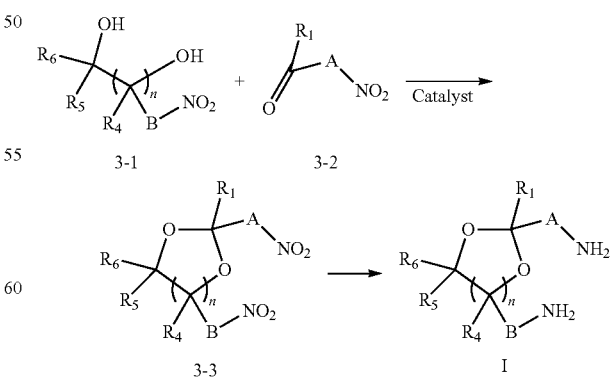

12. The method of claim 11, wherein the catalyst comprises p-toluenesulfonic acid, pyridinium p-toluenesulfonic acid, sulfuric acid, phosphoric acid, nitric acid, hydrogen chloride, molecular sieves, sulfonic acid resin, or solid super acid.

\* \* \* \* \*